United States Patent [19]
Stanley et al.

[11] Patent Number: 6,163,714
[45] Date of Patent: Dec. 19, 2000

[54] OPTICAL SENSOR FOR IN SITU MEASUREMENT OF ANALYTES

[75] Inventors: Christopher John Stanley, Huntingdon, United Kingdom; Anders Weber, Skibby, Denmark

[73] Assignee: Torsana Diabetes Diagnostics A/S, Skodsborg, Denmark

[21] Appl. No.: 09/346,313

[22] Filed: Jul. 2, 1999

[51] Int. Cl.[7] .......................... A61B 5/145; G01N 21/64; G01N 33/53

[52] U.S. Cl. ...................... 600/316; 600/310; 422/82.07; 436/501

[58] Field of Search ..................................... 600/310, 312, 600/316, 317, 322; 604/890.1, 891.1; 422/82.07, 82.08; 435/4, 7.9, 7.72, 7.92; 436/95, 501, 805, 807

[56] References Cited

U.S. PATENT DOCUMENTS

| | | |
|---|---|---|
| 3,996,345 | 12/1976 | Ullman et al. . |
| 4,344,438 | 8/1982 | Schultz . |
| 4,401,122 | 8/1983 | Clark, Jr. . |
| 4,606,351 | 8/1986 | Lübbers . |
| 5,342,789 | 8/1994 | Chick et al. . |
| 5,628,310 | 5/1997 | Rao et al. . |

FOREIGN PATENT DOCUMENTS

| | | |
|---|---|---|
| 2 019 562A | 10/1979 | United Kingdom . |
| WO87/03093 | 5/1987 | WIPO . |
| WO91/09312 | 6/1991 | WIPO . |
| WO94/00602 | 1/1994 | WIPO . |
| WO97/19188 | 5/1997 | WIPO . |
| WO98/55869 | 12/1998 | WIPO . |

OTHER PUBLICATIONS

CRC Press, 1988, p86, Controlled Release Systems: Fabrication technology.

Frank ML and DiMaria C; Drug. Saf. vol. 17 No. 6, Dec. 1997, p. 360–368, "Levonorgestrel subdermal . . . ".

Barnikol WK and Weiler N; Biomed. Tech (Berl). vol. 40 No. 5, May 1995, p. 114–120, "Experiments aimed . . . ".

Wilkins et al; Biosens. Bioelectron vol. 10, No. 5, 1995, p. 485–494, "Integrated implantable device . . . ".

Brunfield et al; Berlin, Jun. 1998, Conference abstract, "A Prototype Transdermal Biosensor".

Jeong et al; Nature 388, Aug. 1997, p. 860–862, "Biodegradable block copolymers as injectable . . . ".

Mansouri and Schultz; Biotechnology, Oct. 1984, p. 885–890, "A Miniature optical glucose sensor . . . ".

Meadows and Schultz; Talanta 35, 1997, p. 1–6, "Fiber-optic Biosensors Based on Fluorescence . . . ".

Jaremko J and Rorstad O; Diabetes Care vol. 21 No. 3, Mar. 1998, p. 444–450, "Advances Toward the Implantable . . . ".

Jackson AJ; Drug Metab. Dispos. vol. 9 No. 6, Jul. 1981, p. 535–540, "Intramuscular Absorption and Regional . . . ".

Tyagi et al; Nature Biotechnology 16, Jan. 1998, p. 49–53, "Multicoulor molecular beacons for allele discrimination".

Fogt EJ; Clin. Chem. vol. 36 No. 8, 1990, p. 1573–80, "Continuous Ex Vivo and In Vivo Monitoring . . . ".

Meadows and Schultz; Anal. Chim Acta 280, 1993, p. 21–30, "Design, manufacture adn characterization of . . . ".

Wilkins E and Atanasov P; Med. Eng. Phys. vol. 18 No. 4, 1996, p. 273–288, "Glucose monitoring: state of . . . ".

The Immunoassay Handbook, ed. David Wild, Macmillan 1994#.

Atsanasov et al Med. Eng. Phys. (1996) 18: 632–640.

*Primary Examiner*—Eric F. Winakur
*Attorney, Agent, or Firm*—Nixon & Vanderhye

[57] ABSTRACT

An implantable sensor for use in the detection or quantitative measurement of an analyte in subcutaneous fluid, the sensor being biodegradable or hydrolysable in vivo. The sensor incorporates an assay for the analyte, the readout of which is a detectable or measurable optical signal which can, when the sensor is in operation in a subcutaneous location, be interrogated transcutaneously by external optical means.

15 Claims, 2 Drawing Sheets

OPTICAL SENSOR FOR IN SITU MEASUREMENT OF ANALYTES

The present invention relates to a sensor for use in the measurement or monitoring of analytes in subcutaneous fluid using optical techniques and to an analyte monitoring system using this sensor. The sensor is particularly suitable for use in situations in which analyte levels must be closely monitored, for example with drugs that must be maintained within a narrow therapeutic window or where analyte measurements must be taken repeatedly, such as in long term diabetes.

In the management of diabetes, the regular measurement of glucose in the blood is essential in order to ensure correct insulin dosing. Furthermore, it has been demonstrated that in the long term care of the diabetic patient better control of blood glucose levels can delay, if not prevent, the onset of retinopathy, circulatory problems and other degenerative diseases often associated with diabetes. Thus there is a need for reliable and accurate self-monitoring of blood glucose levels by diabetic patients.

Currently, blood glucose is monitored by diabetic patients with the use of commercially available colorimetric test strips or electrochemical biosensors (e.g. enzyme electrodes), both of which require the regular use of a lancet-type instrument to withdraw a suitable amount of blood each time a measurement is made. On average, the majority of diabetic patients would use such instruments to take a measurement of blood glucose twice a day. However, the US National Institutes of Health recently recommended that blood glucose testing should be carried out at least four times a day, a recommendation that has been endorsed by the American Diabetes Association. This increase in the frequency of blood glucose testing imposes a considerable burden on the diabetic patient, both in terms of financial cost and in terms of pain and discomfort, particularly in the long term diabetic who has to make regular use of a lancet to draw blood from the fingertips. Thus, there is clearly a need for a better long term glucose monitoring system that does not involve drawing blood from the patient.

There have been a number of recent proposals for glucose measurement techniques that do not require blood to be withdrawn from the patient. Various attempts have been made to construct devices in which an enzyme electrode biosensor is placed on the end of a needle or catheter which is inserted into a blood vessel (Wilkins E and Atanasov P, Med. Eng. Phys (1996) 18: 273–288). Whilst the sensing device itself is located within a blood vessel, the needle or catheter retains connection to the external environment. In practice, such devices are not suitable for use in human patients firstly because the insertion of a needle or catheter into a blood vessel poses an infection risk and is also uncomfortable for the patient and hence not suitable for continuous use. Secondly, devices of this type have not gained approval for use in human patients because it has been suggested that the device itself, on the end of a needle or catheter, may be responsible for the shedding of thromboses into the patient's circulation. This obviously poses a very serious risk to the patient's health.

Mansouri and Schultz (Biotechnology 1984), Meadows and Schultz (Anal. Chim. Acta. (1993) 280: pp 21–30) and U.S. Pat. No. 4,344,438 all describe devices for the in situ monitoring of low molecular weight compounds in the blood by optical means. These devices are designed to be inserted into a blood vessel or placed subcutaneously but require fibre-optic connection to an external light source and an external detector. Again the location of these devices in a blood vessel carries an associated risk of promoting thromboses and in addition, in one embodiment the need to retain a fibre-optic connection to the external environment is impractical for long term use and carries a risk of infection.

In the search for a less invasive glucose monitoring technique some attention has also been focused on the use of infra-red spectroscopy to directly measure blood glucose concentration in blood vessels in tissues such as the ear lobe or finger tip which are relatively 'light transparent' and have blood vessels sited close to the surface of the skin (Jaremko J and Rorstad O, Diabetes Care 1998 21:, 444–450 and Fogt E J, Clin. Chem. (1990) 36:, 1573–80) This approach is obviously minimally invasive, but has proven to be of little practical value due to the fact that the infra-red spectrum of glucose in blood is so similar to that of the surrounding tissue that in practical terms it is virtually impossible to resolve the two spectra.

It has been observed that the concentration of analytes in subcutaneous fluid correlates with the concentration of said analytes in the blood, consequently there have been several reports of the use of glucose monitoring devices which are sited in a subcutaneous location. In particular, Atanasov et al. (Med. Eng. Phys. (1996) 18: pp 632–640) describe the use of an implantable glucose sensing device (dimensions 5.0×7.0×1.5 cm) to monitor glucose in the subcutaneous fluid of a dog. The device consists of an amperometric glucose sensor, a miniature potentiostat, an FM signal transmitter and a power supply and can be interrogated remotely, via antenna and receiver linked to a computer-based data acquisition system, with no need for a connection to the external environment. However, the large dimensions of this device would obviously make it impractical for use in a human patient.

In WO 91/09312 a subcutaneous method and device is described that employs an affinity assay for glucose that is interrogated remotely by optical means. In WO 97/19188 a further example of an implantable assay system for glucose is described which produces an optical signal that can be read remotely. The devices described in WO 91/09312 and WO 97/19188 will persist in the body for extended periods after the assay chemistry has failed to operate correctly and this is a major disadvantage for chronic applications. Removal of the devices will require a surgical procedure.

There remains a clear need for sensitive and accurate blood glucose monitoring techniques which do not require the regular withdrawal of blood from the patient, which do not carry a risk of infection or discomfort and which do not suffer from the practical disadvantages of the previously described implantable devices.

Accordingly, in a first aspect the present invention provides a sensor for the detection or quantitative measurement of an analyte in subcutaneous fluid, the sensor being characterised in that it can function in a subcutaneous location with no physical connection to the external environment, said sensor incorporating an assay for said analyte the readout of which is a detectable or measurable optical signal, which optical signal can, when the sensor is in operation in a subcutaneous location, be interrogated transcutaneously by external optical means and said sensor being biodegradable or hydrolysable in vivo.

The sensor of the invention incorporates assay means for detecting an analyte or for measuring the amount of an analyte, the readout of the assay being an optical signal. Because the sensor is located just under the skin, an optical signal generated in the sensor can be detected transcutaneously (i.e. through the skin) thus obviating the need for any direct connection between the sensor and the external environment. Once the sensor is in place in a subcutaneous location analyte measurements can be taken as often as is necessary with no adverse effects. This is a particular advantage in relation to the long term care of diabetic patients because if glucose measurements are taken more frequently, tighter control can be maintained over the level of glucose in the blood and the risk of developing conditions related to poorly regulated blood glucose, such as retinopathy, arthritis and poor circulation, will be reduced.

Because the sensor of the invention does not itself contain any of the optical components required to interrogate the readout of the assay (these being provided separately and located outside the body) the sensor can easily be provided in a form which is injectable with minimal discomfort to the patient. In a preferred embodiment the components of the assay are incorporated into a matrix material which is permeable to subcutaneous fluid thereby allowing analytes such as glucose to enter the sensor by diffusion and to interact with the components of the assay. The matrix material may be an injectable formulation that forms a gel at the point of injection under the skin of the patient. Alternatively, the sensor may be formed from a solid polymeric matrix material incorporating the components of the assay which is again injected subcutaneously, the polymeric material being of a size suitable for injection through a narrow gauge needle to minimise the discomfort to the patient. When placed subcutaneously the solid polymeric material absorbs water and expands to form a gel thus hydrating the components of the assay.

The device of the present invention is biodegradable or hydrolysable in vivo. In operation, this sensor is placed in a subcutaneous location but then degrades slowly over a period of time. Once the sensor has degraded to an extent that it has ceased to be functionally effective in the monitoring of analytes a fresh sensor can be simply injected or implanted and there is no need for the old sensor to be surgically removed. For reasons of safety, it is desirable that the sensor should degrade into material which is completely eliminated from the body. In practice, this requires that the sensor degrade into materials capable of passing through human kidney membrane to be excreted in urine or which can be metabolised by the body.

As used herein the term 'biodegradable' should be taken to mean that the sensor device of the invention is degraded within the body into materials which can be substantially completely eliminated from the body leaving no residue and that once placed in the body the sensor of the invention becomes degraded to extent that it is substantially completely eliminated from the body within a reasonable timescale relative to the active life-span of the reactive components incorporated into the device. In other words, the sensor device of the invention should ideally be completely eliminated from the body shortly after it has ceased to be effective in accurately measuring/monitoring analyte. Thus, once the sensor ceases to be effective a fresh sensor can simply be put in place and the problem of accumulating old or spent devices within the body will be avoided. Preferably the sensor of the invention will become degraded such that it is substantially completely eliminated from the body over a period of less than one year, more preferably over a period of several months.

Materials suitable for the construction of such a biodegradable sensor include biodegradable block copolymers such as those described by Jeong et al., Nature 388: pp 860–862. Aqueous solutions of these materials are thermosensitive, exhibiting temperature-dependent reversible gel-sol transitions. The polymer material can be loaded with the components of the assay at an elevated temperature where the material forms a sol. In this form the material is injectable and on subcutaneous injection and subsequent rapid cooling to body temperature the material forms a gel matrix. The components of the assay are suspended within this gel matrix which thus constitutes a sensor suitable for detecting or measuring analytes in subcutaneous fluid. Low molecular weight analytes, such as glucose, can freely diffuse into the gel matrix from the surrounding subcutaneous fluid. This particular embodiment of the invention has the advantage that there is no requirement for a surgical procedure for implantation of the sensor. Subcutaneous injection of the sol phase material causes neither significant pain nor tissue damage.

As an alternative to the gel based sensor described above the sensor may be constructed from a solid or gel-like biodegradable polymer matrix material within which the assay components are distributed. When injected or implanted subcutaneously this solid polymer sensor hydrates, swells and analyte penetrates through the structure to encounter the assay components.

In a further embodiment the sensor may be constructed in the form of a hollow chamber, the walls of the chamber being constructed of solid biodegradable polymer material or of a soluble glass and defining a central space in which the components of the assay are contained Low molecular weight analytes are able to diffuse through the chamber walls or through a permeable end plug into the central space and thus come into contact with the components of the assay. The walls of the hollow chamber would gradually degrade over time.

Both the solid polymer sensors and the hollow chamber sensors may be introduced into a subcutaneous location by implantation or injection, injection being preferred for sensors with a diameter of less than 2 mm. Both types of sensors can be formed in a wide variety of geometric shapes as desired prior to injection or implantation, cylindrical sensors being particularly preferred.

Biodegradable materials suitable for use in the construction of the hollow chamber and solid polymer sensors include cross-linked proteins such as human albumin, fibrin gels, polysaccharides such as starch or agarose, poly (DL-lactide) and poly (DL-glycolide), polyanhydrides, fatty acid/cholesterol mixtures that form semi-solid derivates, hyaluronates and liquid crystals of monooliein and water.

In a still further embodiment, the sensor may be formed as a suspension of microparticles of preferred dimeter <100 $\mu$m each of which contains the assay components either encapsulated inside a hollow microparticle, or dispersed within the material of a solid microparticle. Such a suspension of microparticles is readily injected subcutaneously. Preferably the microparticles are formed from a material which is biodegradable or hydrolysable in vivo. Alternatively, liposomes containing the assay components can be used. Liposomes of diameter 0.3 to 2.0 $\mu$m have been shown to remain at the site of injection (Jackson A J., Drug Metab. Dispos. 1981 9, 535–540) so they would be suitable for use in the sensor. In a further embodiment the sensor comprises a plurality of empty erythrocytes which have been loaded with assay components and then injected subcutaneously. Empty erythrocytes, also known as erythrocyte ghosts, can be prepared by exposing intact erythrocytes to a hypotonic solution so that they swell and burst to release their cytoplasmic contents. The empty erythrocytes can then be loaded with assay components before allowing the plasma membranes to re-seal.

In the preferred embodiments of the sensor (i.e. gel, solid polymer, hollow chamber, or microparticles) it is advantageous for the assay components to have a restricted diffusion in order to minimise their loss from the sensor. This can be achieved by ensuring that the gel or the biodegradable material has a pore size that permits the diffusion of low molecular weight analytes but not the assay components themselves. These would only be lost as the material or gel degrades over time. The assay components are preferably of high molecular weight, such as proteins or polymers, in order to restrict their loss from the sensor.

There are several different mechanisms by which a biodegradable sensor can be degraded into materials which can be eliminated from the body, including hydrolysis, dissolution and cleavage of susceptible bonds by enzymic action, including the action of components of the immune system. The mechanism of degradation is ultimately dependent on the nature of the material from which the sensor is constructed. For example, most biodegradable polymer materials, such as polylactides and polyglycolides, are hydrolysable by water. A sensor device comprising a matrix of hydrolysable polymer in which the reactive components of the assay are embedded therefore degrades as a result of hydrolysis of the matrix, gradually releasing the reactive components. The overall time taken for the matrix to degrade will generally be dependent on the concentration of polymer in the matrix material and on the overall dimensions of the sensor. Once released from the matrix material, the reactive components of the assay, being protein or carbohydrate based, are either taken up by the liver and thereby removed or broken down in situ by the action of enzymes.

Assays suitable for use in the sensor include reactions such as hydrolysis and oxidation leading to a detectable optical change i.e. fluorescence enhancement or quenching which can be observed transcutaneously. A preferred assay for use in the sensor of the invention is a binding assay, the readout of which is a detectable or measurable optical signal which can be interrogated transcutaneously using optical means. The binding assay generating the optical signal should preferably be reversible such that a continuous monitoring of fluctuating levels of the analyte can be achieved. This reversibility is a particular advantage of the use of a binding assay format in which the components of the assay are not consumed. Binding assays are also preferred for use in the sensor of the invention for reasons of safety as they cannot generate any unwanted products as might be generated by an enzymatic or electrochemical reaction.

Preferred binding assay configurations for use in the sensor of the invention include a reversible competitive, reagent limited, binding assay, the components of which include an analyte analog and an analyte binding agent capable of reversibly binding both the analyte of interest and the analyte analog. The analyte of interest and the analyte analog compete for binding to the same binding site on the analyte binding agent. Such competitive binding assay configurations are well known in the art of clinical diagnostics and are described, by way of example, in The Immunoassay Handbook, ed. David Wild, Macmillan Press 1994. Suitable analyte binding agents for use in the assay would include antibodies or antibody fragments which retain an analyte binding site (e.g Fab fragments), lectins (e.g. concanavalin A), hormone receptors, drug receptors, aptamers and molecularly-imprinted polymers. Preferably the analyte analog should be a substance of higher molecular weight than the analyte such that it cannot freely diffuse out of the sensor. For example, an assay for glucose might employ a high molecular weight glucose polymer such as dextran as the analyte analog.

Suitable optical signals which can be used as an assay readout in accordance with the invention include any optical signal which can be generated by a proximity assay, such as those generated by fluorescence energy transfer, fluorescence polarisation, fluorescence quenching, phosphorescence techniques, luminescence enhancement, luminescence quenching, diffraction or plasmon resonance, all of which are known per se in the art.

The most preferred embodiment of the sensor of the invention incorporates a competitive, reagent limited binding assay which generates an optical readout using the technique of fluorescence energy transfer. In this assay format the analyte analog is labelled with a first chromophore (hereinafter referred to a the donor chromophore) and the analyte binding agent is labelled with a second chromophore (hereinafter referred to as the acceptor chromophore). It is an essential feature of the assay that the fluorescence emission spectrum of the donor chromophore overlaps with the absorption spectrum of the acceptor chromophore, such that when the donor and acceptor chromophores are brought into close proximity by the binding of the analyte analog to the analyte binding agent a proportion of the fluorescent signal emitted by the donor chromophore (following irradiation with incident radiation of a wavelength absorbed by the donor chromophore) will be absorbed by the proximal acceptor chromophore, a process known in the art as fluorescence energy transfer, with the result that a proportion of the fluorescent signal emitted by the donor chromophore is quenched and, in some instances, that the acceptor chromophore emits fluorescence. Fluorescence energy transfer will only occur when the donor and acceptor chromophores are brought into close proximity by the binding of analyte analog to analyte binding agent. Thus, in the presence of analyte, which competes with the analyte analog for binding to the analyte binding agent, the amount of quenching is reduced (resulting in a measurable increase in the intensity of the fluorescent signal emitted by the donor chromophore or a fall in the intensity of the signal emitted by the acceptor chromophore) as labelled analyte analog is displaced from binding to the analyte binding agent. The intensity of the fluorescent signal emitted from the donor chromophore thus correlates with the concentration of analyte in the subcutaneous fluid bathing the sensor.

An additional advantageous feature of the fluorescence energy transfer assay format arises from the fact that any fluorescent signal emitted by the acceptor chromophore following excitation with a beam of incident radiation at a wavelength within the absorption spectrum of the acceptor chromophore is unaffected by the fluorescence energy transfer process. It is therefore possible to use the intensity of the fluorescent signal emitted by the acceptor chromophore as an internal reference signal, for example in continuous calibration of the sensor or to monitor the extent to which the sensor has degraded and thus indicate the need to implant or inject a fresh sensor. As the sensor degrades, the amount of acceptor chromophore present in the sensor will decrease and hence the intensity of fluorescent signal detected upon excitation of the acceptor chromophore will also decrease. The fall of this signal below an acceptable baseline level would indicate the need to implant or inject a fresh sensor.

Competitive binding assays using the fluorescence energy transfer technique which are capable of being adapted for use in the sensor of the invention are known in the art. U.S. Pat. No. 3,996,345 describes immunoassays employing antibodies and fluorescence energy transfer between a fluorescer-quencher chromophoric pair. Meadows and Schultz (Anal. Chim. Acta (1993) 280: pp 21–30)

describe a homogeneous assay method for the measurement of glucose based on fluorescence energy transfer between a labelled glucose analog (FITC labelled dextran) and a labelled glucose binding agent (rhodamine labelled concanavalin A). In all of these configurations the acceptor and donor chromophores/quenchers can be linked to either the binding agent or the analyte analog.

An alternative to the fluorescence energy transfer is the fluorescence quenching technique. In this case a compound with fluorescence quenching capability is used instead of the specific acceptor chromophore and the optical signal in a competitive binding assay will increase with increasing analyte. An example of a powerful and non-specific fluorescence quencher is given by Tyagi et al. Nature Biotechnology (1998) 18: p 49.

The sensor of the invention can be adapted for the detection or quantitative measurement of any analyte present in subcutaneous fluid. Preferred analytes include glucose (in connection with the long-term monitoring of diabetics), urea (in connection with kidney disease or disfunction), lactate (in connection with assessment of muscle performance in sports medicine), ions such as sodium, calcium or potassium and therapeutic drugs whose concentration in the blood must be closely monitored, such as, for example, digoxin, theophylline or immunosuppressant drugs. The above analytes are listed by way of example only and it is to be understood that the precise nature of the analyte to be measured is not material to the invention.

The sensor is interrogated transcutaneously using optical means i.e. no physical connection is required between the sensor and the optical means. When the sensor incorporates a competitive, reagent limited, binding assay employing the technique of fluorescent energy transfer, the optical means should supply a first beam of incident radiation at a wavelength within the absorption spectrum of the donor chromophore and preferably a second beam of incident radiation at a wavelength within the absorption spectrum of the acceptor chromophore. In addition, the optical means should be capable of measuring optical signals generated in the sensor at two different wavelengths; wavelength 1 within the emission spectrum of the donor chromophore (the signal generated in connection with the measurement of analyte and wavelength 2 in the emission spectrum of the acceptor chromophore (which could be the analyte signal or the internal reference or calibration signal).

Optical means suitable for use in remote interrogation of the device of the invention include a simple high-throughput fluorimeter comprising an excitation light source such as, for example, a light-emitting diode (blue, green or red >1000 mCa), an excitation light filter (dichroic filter), a fluorescent light filter (dichroic or dye filter) and a fluorescent light detector (PIN diode configuration). A fluorimeter with these characteristics may exhibit a sensitivity of between picomolar to femtomolar fluorophore concentration.

A suitable fluorimeter set-up is shown in the accompanying FIG. 1 and described in the Examples included herein. The fluorimeter separately measures the following parameters:

At wavelength 1 (donor chromophore)
  Excitation light intensity, I(1,0)
  Ambient light intensity, I(1,1)
  Intensity of combined fluorescent and ambient light, I(1,2)
At wavelength 2 (acceptor chromophore)
  Excitation light intensity, I(2,0)
  Ambient light intensity, I(2,1)
  Intensity of combined fluorescent and ambient light, I(2,2)

Measurements are taken by holding the fluorimeter close to the skin and in alignment with the sensor. When making transcutaneous measurements of the fluorescent signals generated in the sensor it is necessary to take account of the absorption of signal by the skin, the absorptivity of human skin is found by experiment to be lowest in the range from 400 nm to 900 nm. The final output provided is the normalized ratio between the fluorescent intensity from the two fluorophores, defined by the following relation (Equation 1):

$$\frac{(I(1,2)-I(1,1))\ I(2,0)}{(I(2,2)-I(2,1))\ I(1,0)} \quad (1)$$

In a third aspect the invention provides an analytical system suitable for the detection or quantitative measurement of an analyte in subcutaneous fluid, said analytical system comprising,
  (i) a sensor for the detection or quantitative measurement of an analyte in subcutaneous fluid in accordance with the first aspect of the invention;
  (ii) optical means suitable for the transcutaneous interrogation of the sensor of (i).

In a fourth aspect the invention provides a method of detecting or quantitatively measuring an analyte in the subcutaneous fluid of a mammal, which method comprises the steps of,
  (a) injecting or implanting a sensor for the detection or quantitative measurement of an analyte in subcutaneous fluid in accordance with the first aspect of the invention;
  (b) allowing the assay of said sensor to reach thermodynamic equilibrium;
  (c) interrogating the readout of said assay using optical means; and
  (d) relating the measurement obtaining in (c) to the concentration of analyte.

The final output from the optical means (e.g. the fluorimeter) as given by Equation 1 above is converted to analyte concentration preferably by means of a computer using calibration data which can be obtained based on the principles set out below.

A calibration curve can be established empirically by measuring response versus analyte concentration for a physiologically relevant range of analyte concentrations. Preferably this takes place in vitro as part of the production of the sensor device. The calibration procedure can be simplified considerably by using the mathematical relation between response and analyte concentration in a competitive affinity sensor which is derived as follows:

The response of a competitive affinity sensor is governed by the reactions:

$$RC \rightarrow R+C$$

$$RL \rightarrow R+L$$

designating the dissociation of the complexes RC and RL, formed by the combination of analyte binding agent (R) with analyte (L) or analyte analog (C).

The corresponding dissociation equilibrium constants are:

$$K_1 = \frac{C_R C_C}{C_{RC}}$$

and, $$K_2 = \frac{C_R C_L}{C_{RL}}$$

where C designates the number of moles of the species in the sensor divided by the sensor volume. Using this measure of concentration both immobilized species and species in solution are treated alike.

The mass balance equations are:

$$T_C = C_C + C_{RC}$$

for total analyte analog concentration and, $$T_R = C_R + C_{RC} + C_{RL}$$

for total analyte binding agent concentration.
Using the expression above, the relation between response and analyte concentration is derived:

$$\frac{T_c - C_c}{C_c} K_1 = \frac{T_R - (T_c - C_c)}{1 + (C_L/K_2)} \qquad (2)$$

By using this relation the amount of data necessary for the calibration can be reduced to two key parameters: Total analyte binding agent concentration and total analyte analog concentration. The calibration curve is thus determined by two points on the curve.

The present invention will be further understood with reference to the following non-limiting Examples, together with the accompanying Figures in which.

EXAMPLE 1

Figure 1:
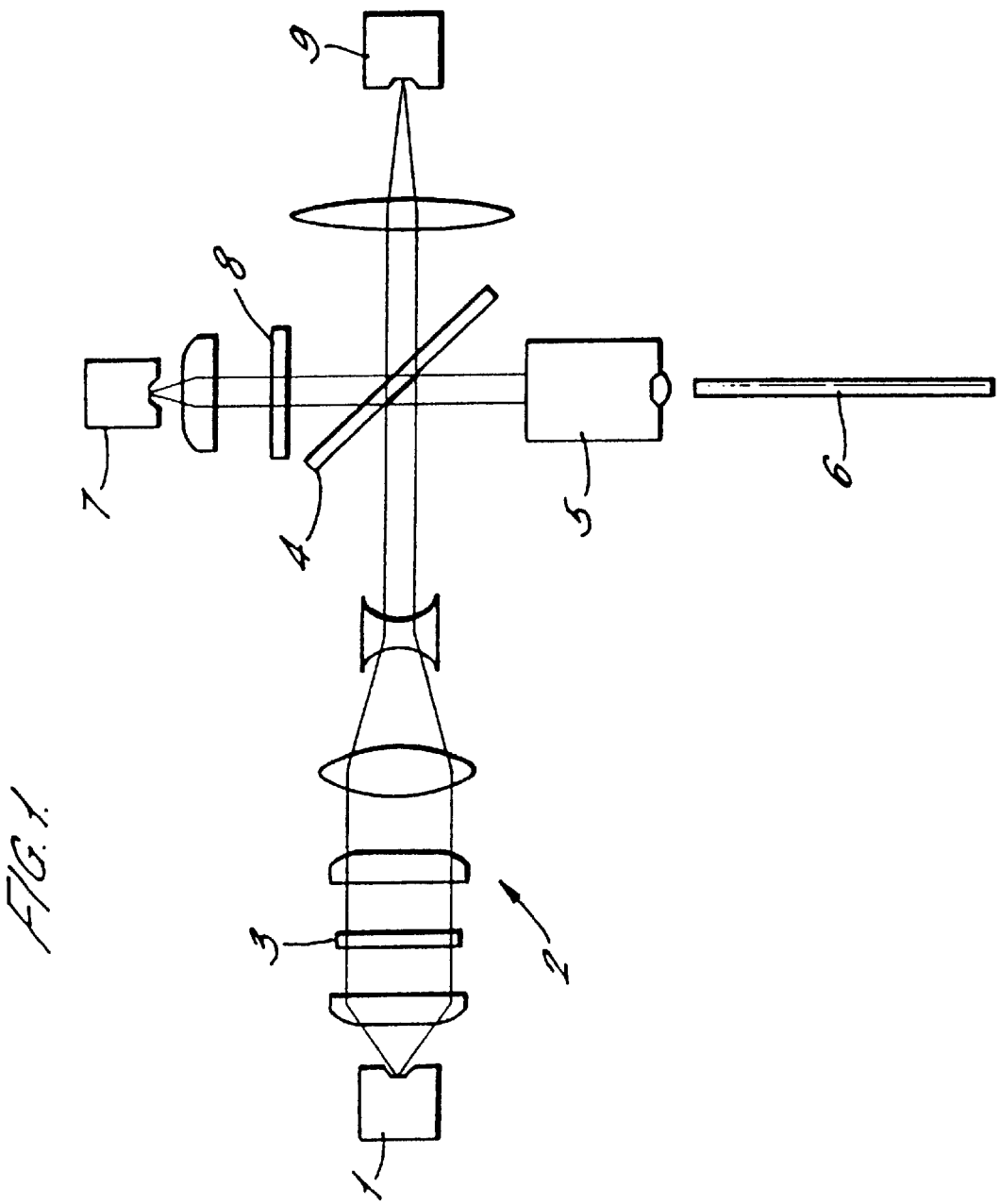
FIG. 1 is a schematic diagram of the optical part of a fibre optic fluorimeter.

A glucose assay according to Meadows and Schultz (Talanta, 35, 145–150, 1988) was developed using concanavalin A-rhodamine and dextran-FITC (both from Molecular Probes Inc, Oregon, USA). The principle of the assay is fluorescence resonance energy transfer between the two fluorophores when they are in close proximity; in the presence of glucose the resonance energy transfer is inhibited and the fluorescent signal from FITC (fluorescein) increases. Thus increasing fluorescence correlates with increasing glucose. The glucose assay was found to respond to glucose, as reported by Schultz, with approximately 50% recovery of the fluorescein fluorescence signal at 20 mg/dL glucose. Fluorescence was measured in a Perkin Elmer fluorimeter, adapted for flow-through measurement using a sipping device.

EXAMPLE 2

The glucose assay components of Example 1 were added to stirred solutions (1 ml) of 1%, 1.5% and 2% w/v of a low melting temperature agarose (Type IX, Sigma, St. Louis, USA) at 45° C. After dispersal, the temperature was reduced to 20° C. and the stirring was stopped. When the gel had formed (after approximately 3 hours) it was placed in a ceramic mortar and ground to a particle size of 50 to 100 µm, by visual reference to a polystyrene bead preparation with the same diameter. The particle preparation was suspended in 0.9% w/v saline and filtered through a nylon mesh to remove the larger particles. The particles that passed through the mesh were then centrifuged in a bench centrifuge at 500 g and the supernatant containing fines was discarded. During the process the particles retained their fluorescence by visual inspection and by measurement of the rhodamine fluorescence in the Perkin Elmer fluorimeter. Adding glucose at 20 mg/dL to a sample of the suspended particles resulted in a rise in the fluorescein fluorescence signal over a 30 minute period. Thus the assay components contained within the agarose gel were responsive to glucose.

The glucose assay chemistry components are inherently biodegradable (or excretable) in the human body since they are based on peptide and carbohydrate materials. Degradation by enzyme digestion and/or simple transport to the liver or kidney will ensure that the assay components will be removed from the body following implantation or subcutaneous injection.

EXAMPLE 3

1 ml samples of the agarose particle suspensions containing glucose assay reagents (described in Example 2) were placed in a water bath at 37° C. to simulate human body temperature. Over the following six weeks the particle structure was lost as the structures degraded, with the higher concentration gels exhibiting the slowest degradation. The light scattering signal measured using the fluorimeter also fell as the particles dispersed, indicating degradation of the particles. This experiment simulates conditions in the human body—it is expected that the particles will eventually be cleared from the site of injection and the assay chemistry components will be degraded either in situ or transported to the liver for further processing, or excreted in the urine.

EXAMPLE 4

Figure 2:
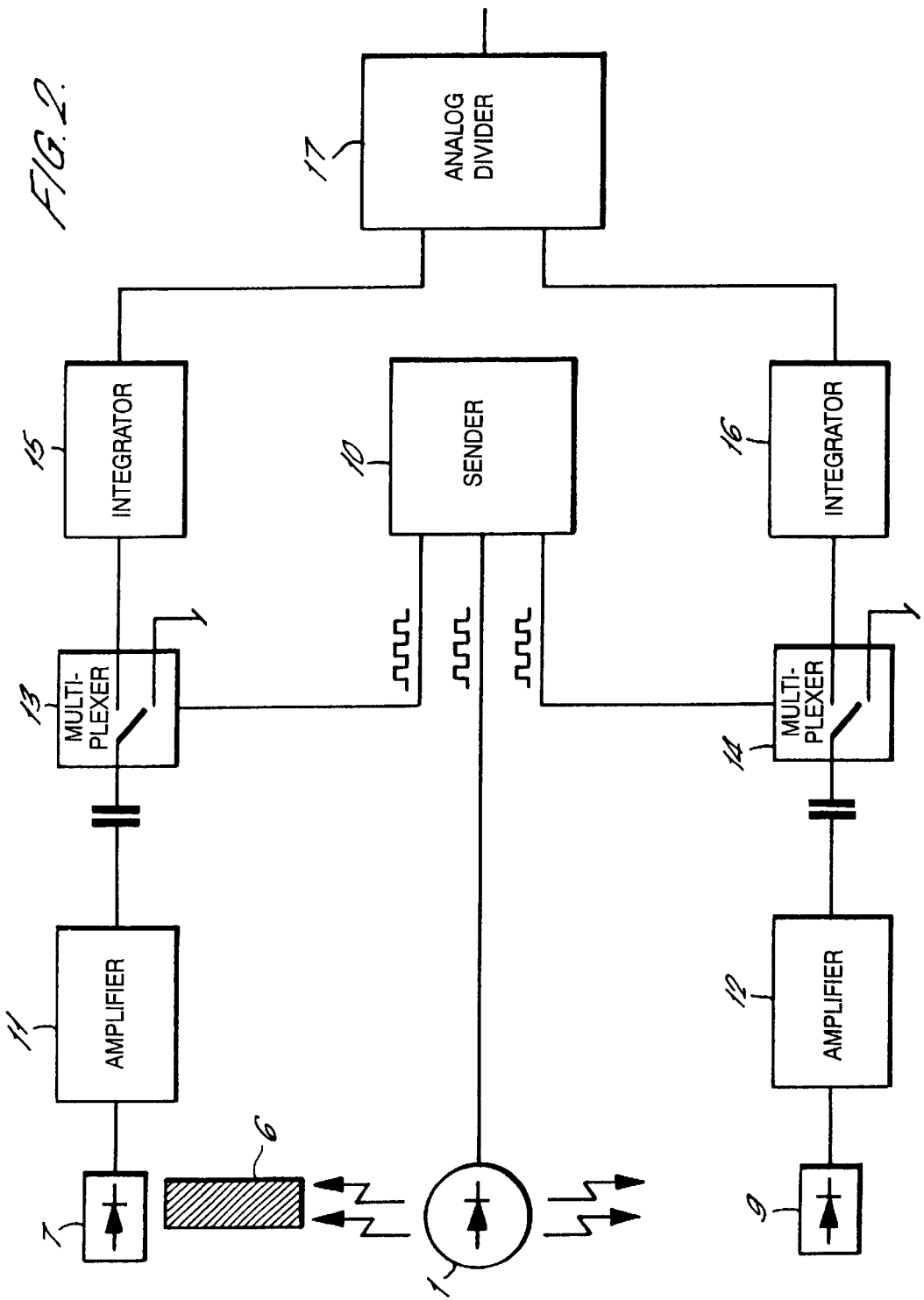
FIG. 2 is a schematic diagram of a driver/amplifier circuit used in conjunction with the optical part of the fibre optic fluorimeter.

A fibre optic spectrometer was assembled as follows:

The optical part of a fibre optic fluorimeter was made from standard components on a micro bench. The setup, comprising a red LED as light source, lenses, dichroic beamsplitter and filters and detector diodes, was as shown in FIG. 1. Briefly, the fluorimeter comprises a light-emitting diode (1) providing an excitation light beam which passes through a condenser (2) containing an excitation filter (3) and is incident upon a beamsplitter (4). Part of the excitatory beam is thereby deflected into launching optics (5) and enters an optical fibre (6). When the fluorimeter is in use in the interrogation of a subcutaneously located sensor the end of optical fibre (6) is positioned close to the surface of the skin, in alignment with the subcutaneous sensor, so that beam of excitatory light is incident upon the sensor. A portion of the optical signal emitted from the sensor following excitation enters the optical fibre (6) and is thereby conveyed into the fluorimeter where it passes through a blocking filter (8) and is measured by a signal detector diode (7). The fluorimeter also contains a reference detector diode (9) which provides a reference measurement of the excitatory light emitted from the LED (1). The ends of a 1 m long Ensign Beckford optical fibre, 0.5 mm in diameter, numerical aperture of 0.65, were around to a mirror finish using diamond paste on glass paste. One end of the fibre was mounted in an X Y Z holder in front of a 20 x microscope objective. The diodes (LED (1) and detector diodes (7) and (9)) were connected to a custom made driver/amplifier circuit as shown in FIG. 2. The circuit comprises a sender (10), current amplifiers (11) and (12), multiplexers (13) and (14), integrators (15) and (16) and analog divider (17). The driver circuit was set to drive the LED (1) at 238 Hz and the signals from the detector diodes (7) and (9) were switched between ground and the storage capacitors (integrator with a time constant of 1 second) synchronised with the driver signal. The two integrated signals correspond to background-corrected fluorescent signal and background corrected excitation light level (LED intensity). The former divided by the latter was supported by an analog divider as shown in FIG. 2. For test purposes, the distal end of the fibre (6) was dipped into dilute solutions of rhodamine and the optics were adjusted for maximum signal from the analog divider.

The fluorimeter/spectrometer is battery operated (typical power consumption 150 mA at 9V) and for convenience can be constructed in the shape and dimensions of a pen.

EXAMPLE 5

1.5% w/v agarose particles of approximately 50 μm diameter containing the assay components (as described in Example 2) were washed several times by centrifuging and resuspending in 0.9% w/v saline solution. This washing procedure removed excess reagents that were not trapped within the gel structure. The particles remained highly fluorescent during this process. Then the particle suspension was loaded into a standard disposable syringe (Becton Dickinson, USA) and injected subcutaneously under the skin on the back of the hand of a human volunteer. A fibre optic spectrometer (see Example 4) was directed at the skin and a rhodamine fluorescence signal was obtained, indicating that transdermal measurements can be made on implanted biodegradable sensors.

EXAMPLE 6

A glass capillary of dimensions 10 mm×2 mm composed of a phosphate based soluble glass (Pilkington CRS, Wrexham, UK) was part-filled with a solution of glucose assay reagents. The ends of the capillary were then sealed by dipping in a solution of 1% w/v low melting temperature agarose heated to 45° C. and then cooling to room temperature (22° C.). Both ends of the capillary were sealed in this manner. The sealed capillary was placed on a flat surface and the fibre optic spectrometer (see Example 4) was positioned to take a fluoresence reading of the contents. The strong rhodamine fluorescence indicated that reagents had been incorporated into the capillary. The capillary was then placed in a top-stirred solution of 20 mg/dL glucose in 0.9% w/v saline for 16 hours at room temperature (22° C.). The capillary was then removed from the glucose solution, the external surface was dried and the capillary was placed on a flat surface. A reading with the fibre optic spectrometer indicated that an increase in fluorescein fluorescence had occurred, showing that glucose had penetrated the capillary by diffusion through the agarose gel caps. The capillary was then replaced in the top-stirred 0.9% w/v saline solution at 37° C. After 200 hours the structure of the capillary had begun to collapse as the phosphate glass wall was breached and the contents were released into the surrounding fluid. After a further 20 days no residue of the glass capillary structure remained and the agarose gel caps had also dissolved. Thus the entire capillary based sensor was shown to be fully degradable under physiological conditions.

What is claimed is:

1. A sensor for the detection or quantitative measurement of an analyte in subcutaneous fluid, said sensor being characterised in that it can function in a subcutaneous location with no physical connection to the external environment, said sensor incorporating an assay for said analyte the readout of which is a detectable or measurable optical signal, which optical signal can, when the sensor is in operation in a subcutaneous location, be interrogated transcutaneously by external optical means and said sensor being biodegradable or hydrolysable in vivo.

2. A sensor as claimed in claim 1 wherein said assay is a binding assay, the readout of which is a detectable or measurable optical signal.

3. A sensor as claimed in claim 2 wherein said binding assay is a competitive binding assay the components of which include an analyte binding agent and an analyte analog.

4. A sensor as claimed in claim 3 wherein said analyte analog is labelled with a first chromophore and said analyte binding agent is labelled with a second chromophore, the emission spectrum of said first chromophore overlapping with the absorption spectrum of said second chromophore.

5. A sensor as claimed in claim 3 wherein the binding agent is an antibody, an Fab fragment, a lectin, a hormone receptor, a drug receptor, an aptamer or a molecularly-imprinted polymer.

6. A sensor as claimed in claim 2, wherein said detectable or measurable optical signal is generated by fluorescence energy transfer, fluorescence polarisation, fluorescence quenching, phosphorescence, luminescence enhancement, luminescence quenching, diffraction or plasmon resonance.

7. A sensor as claimed in claim 1, which comprises an injectable or implantable matrix material, the components of said assay being suspended in said matrix material.

8. A sensor as claimed in claim 1, which comprises a plurality of microparticles.

9. A sensor as claimed in claim 8 wherein said microparticles are solid microparticles and the components of said assay are uniformly dispersed in said solid microparticles.

10. A sensor as claimed in claim 8 wherein said microparticles are hollow microparticles and the components of said assay are encapsulated inside said hollow microparticles.

11. A sensor as claimed in claim 1, which comprises a plurality of liposomes, the components of said assay being encapsulated inside said liposomes.

12. A sensor as claimed in claim 1, which comprises a hollow chamber having a wall portion enclosing a central space containing the components of said assay means.

13. A sensor as claimed in claim 1, which comprises a plurality of empty erythrocytes which have been loaded with the components of said assay.

14. An analytical system for the detection or quantitative measurement of an analyte in subcutaneous fluid,, which analytical system comprises a sensor as claimed in claim 1, together with optical means suitable for the trans-cutaneous interrogation of said sensor.

15. A method of detecting or quantitatively measuring an analyte in the subcutaneous fluid of a mammal, which method comprises the steps of:

(a) injecting or implanting a sensor for the detection or quantitative measurement of an analyte in subcutaneous fluid as claimed in claim 1 into a subcutaneous location on said mammal;

(b) allowing the assay of said sensor to reach thermodynamic equilibrium;

(c) interrogating the readout of said assay using optical means; and (d) relating the measurement obtained in (c) to the concentration of analyte.

* * * * *